United States Patent [19]
Westley

[11] 4,076,834
[45] Feb. 28, 1978

[54] THERAPEUTIC AGENTS FOR IMPROVING CARDIOVASCULAR FUNCTION

[75] Inventor: John Westley, Mountain Lakes, N.J.

[73] Assignee: Hoffmann-La Roche Inc., Nutley, N.J.

[21] Appl. No.: 642,226

[22] Filed: Dec. 19, 1975

Related U.S. Application Data

[62] Division of Ser. No. 489,977, Jul. 19, 1974, abandoned.

[51] Int. Cl.$^2$ .............................................. A61K 31/35
[52] U.S. Cl. .................................................... 424/283
[58] Field of Search ................................. 424/283, 122

[56] References Cited

U.S. PATENT DOCUMENTS 3,627,883  12/1971  Gorman ............................... 424/122

Primary Examiner—Jerome D. Goldberg
Attorney, Agent, or Firm—Samuel L. Welt; Bernard S. Leon; William M. Farley

[57] ABSTRACT

Methods of, and compositions for, improving cardiovascular function utilizing as the active agent certain polyether antibiotics, their pharmaceutically acceptable salts and derivatives are disclosed.

1 Claim, No Drawings

THERAPEUTIC AGENTS FOR IMPROVING CARDIOVASCULAR FUNCTION

This is a division of application Ser. No. 489,977 filed July 19, 1974 and now abandoned.

DESCRIPTION OF THE INVENTION

Certain polyether antibiotics, their pharmaceutically acceptable salts and derivatives have been discovered to possess cardiovascular-effecting properties in mammals. More particularly, we have discovered that these compounds cause a myocardial stimulation.

The polyether antibiotics which cause myocardial stimulation include nigericin, monensin and X-206 as well as their pharmaceutically acceptable salts. All these antibiotics are known and publications directed to their preparation are as follows:

Nigericin has been known for some time under the names helixin C, antibiotic X-464, antibiotic K-178, polyetherin A, and azalomycin M. Its structure was characterized by Steinrauf et al., Biochemical and Biophysical Research Communications 33, 29 (1968). Its structure formula is depicted below:

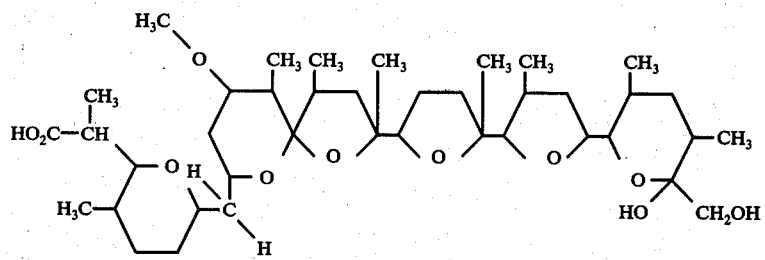

Harned et al., Antibiotic and Chemotherapy I, 594–96 (1951) originally mentioned nigericin. It was also described by Gorman et al., U.S. Pat. No. 3,555,510.

The organism which produces nigericin is a strain of *Streptomyces violaceoniger* which is on unrestricted deposit under the identification number NRRL B1356 in the Northern Research and Utilization Development Division, Agricultural Research Service, U.S. Department of Agriculture, Peoria, Ill. The preparation of nigericin is described in U.S. Pat. No. 3,794,732.

Monensin was described by Haney et al., U.S. Pat. No. 3,501,568. The substance known as monensin is actually a mixture of four components. These four components are included in the term "monensin" as used herein. The structural formula indicated below is the acid form of the component A of monensin.

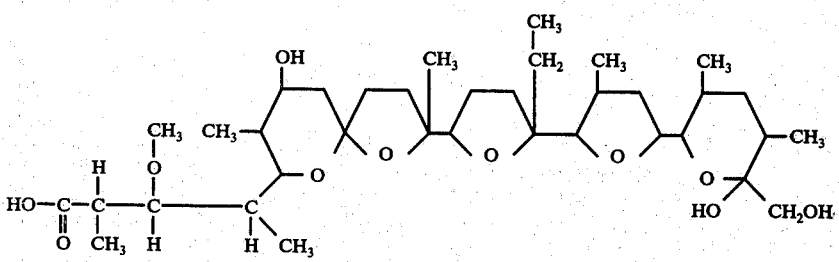

Monensin is the fermentation product of an organism which can be found on unrestricted deposit under the number ATCC 15413 in the American Type Culture Collection, Rockville, Md.

The antibiotic X-206 was reported for the first time in 1951 by Berger et al., JACS 73, 5295-98 (1951). The Streptomyces organism form which one is able to obtain antibiotic X-206 is available at Center International d'Information sur Les Antibiotiques (International Center for Information on Antibiotics) Liege, Belgium, which lists the organism on page 31 of its Bulletin No. 3 (1966). X-206 is characterized as having a molecule very similar to those of other antibiotic compounds useful in the present process. Its formula has been depicted by Blount et al., Chemical Communications, 1971, 927–928 as follows:

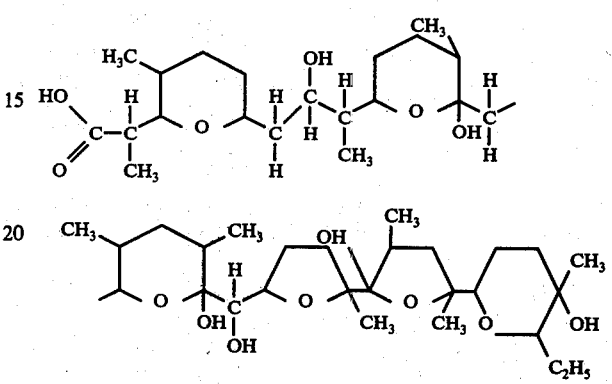

A method for the preparation of X-206 is shown in U.S. Pat. No. 3,794,732.

The polyether antibiotics of this invention are all acids and react with organic and inorganic bases to form a variety of pharmaceutically acceptable salts. These salts are prepared from the free acid by methods well known in the art, for example, by reacting the free acid in solution with a suitable base or salt. Examples of pharmaceutically acceptable basic substances capable of forming salts for the purpose of the present invention include alkali metal bases, such as sodium hydroxide, potassium hydroxide, lithium hydroxide and the like; alkaline earth metal bases, such as calcium hydroxide, barium hydroxide and the like; and ammonium hydroxide. Alkali metal or alkaline earth metal salts suitable for forming pharmaceutically acceptable salts can include anions such as carbonates, bicarbonate and sulfates.

Examples of organic bases forming pharmaceutically acceptable salts with the antibiotics are lower alkyl amines, primary, secondary and tertiary hydroxy-lower alkylamines such as ethylamine, isopropylamine, diethylamine, methyl-n-butylamine, ethanolamine and diethanolamine.

An amine especially preferred is N-methylglucamine. Salts of N-methylglucamine are of special value because of their water-solubility which makes them amenable to parenteral use. The preparation of these salts and their water-solubility, included here for completeness although not part of this invention, is disclosed and claimed in U.S. patent application Ser. No. 489,976 filed on even date and entitled "Solubilization of Polyether Antibiotics, Their Derivatives, Isomers and Homologs in Aqueous Systems " by H. Newmark and J. Westley.

Representative of such N-methylglucamine salts are:

Antibiotic X-206, di-(N-methylglucamine) salt
Antibiotic X-464 (Nigericin), di-(N-methylglucamine)-salt
Monensin, di-(N-methylglucamine)salt
Antibiotic X-206, mono-(N-methylglucamine)salt
Antibiotic X-464 (Nigericin), mono-(N-methylglucamine)salt
Monensin, mono-(N-methylglucamine)salt Active compounds for therapeutic treatment by improving cardiovascular function which include lasalocid, its salts, derivatives, isomers and homologs are described in copending patent application Ser. No. 348,809, filed Apr. 6, 1973 and entitled "A Therapeutic Agent for Improving Cardiovascular Function" by B. Pressman and N. De Guzman and Ser. No. 489,978 filed on even date herewith and entitled "Therapeutic Agents for Improving Cardiovascular Function" by J. Westley.

The most significant desired criteria for chemical compounds used to treat chronic heart conditions, such as congestive heart failure, or emergency heart conditions, e.g., shock, heart failure, are that the compound should have a positive inotropic effect with little or no chronotropic effects and display minimal, if any, adrenergic action. Other desirable criteria are that the compounds have a rapid onset of action, require a small effective dose, are non-toxic at the effective doses, display a satisfactory duration of action, display a return to the original pre-drug values of cardiovascular activity, and continued identical response to subsequently repeated identical doses. It is also desirable that such compounds be amenable to oral or parenteral administration. The oral administration is particularly preferred for long term treatment of chronic diseases, e.g. congestive heart failure, while parenteral administration is the choice for emergency treatment, e.g., shock, acute heart failure.

The active compounds of this invention fulfill the desired criteria and are thus useful for stimulation of cardiovascular functions and treating such ailments as cardiogenic shock, septic shock and congestive heart failures.

For use as cardiovascular agents, the active agents are formulated, using conventional inert pharmaceutical adjuvant materials, into dosage forms which are suitable for oral or parenteral administration. Such dosage forms include tablets, suspensions, solutions, hard or soft capsules, dragees and the like. The identity of the inert adjuvant materials which are used in formulating the active compounds into oral and parenteral dosage forms will be immediately apparent to persons skilled in the art. These adjuvant materials, either inorganic or organic in nature, include, for example, water, dimethylsulfoxide, gelatin, albumin, lactose, starch, magnesium stearate, preservatives, stabilizers, wetting agents, emulsifying agents, salts for altering osmotic pressure, buffers, etc. which can be incorporated, if desired, into such formulations.

The quantity of active agent which is present in any of the above described dosage forms generally varies from 5 to 100 mg. per unit dosage. The dosage administered to a particular patient is variable, depending upon the clinician's judgment using as the criteria the condition and size of the patient, the potency of the active agent and the patient's response thereto. An effective dosage amount of active agent can therefore only be determined by the clinician utilizing his best judgment on the patient's behalf.

Generally, parenteral doses should be from about 20 mg. to about 50 mg. for the average size man. Smaller persons or larger persons require adjustments due to size. Oral doses, usually capsules, but tablets can be used, generally are about twice the parenteral dose.

The frequency of the dose would depend upon the patient's condition. Chronically ill patients may require administration every 2 to 3 hours or once a day, depending on the severity of the disease and the patient's response.

Emergency patients frequently need only one dose of active compound, particularly those in shock.

The cardiovascular effects of the various derivatives of lasalocid are manifested by positive inotropic effects with minimal chronotropic effects. These effects are measured by the parameters of myocardial force of contraction, heart rate and arterial blood pressure. To obtain these measurements, dogs were anesthetized and catheters were introduced into the femoral artery and vein for recording femoral arterial blood pressure and for drug administration, respectively.

For example, Beagle hounds of either sex were anesthetized with intravenously administered thiopental sodium (15 mg/kg) and barbital sodium (275 mg/kg). Artificial respiration was maintained during surgical manipulation by using a Bird respirator (Mark 8 ). Myocardial force of contraction was measured by suturing a strain gauge arch to the surface of the right ventricle after opening the chest through the left 4th interspace. [This procedure is described by Boniface et al., Resistance strain gauge arches for direct measurement of heart force in animals, Proc. Soc. Exp. Biol. Med., 84:263–266 (1953).] The chest was then closed by suturing. Pneumothorax was reduced and spontaneous breathing was permitted.

Exlectrocardiograms were recorded using lead 11. Heart rates were recorded on a Sanborn cardiotachometer by using the electrical signal of the "R" wave of lead 11. A Statham pressure transducer measured femoral artery blood pressure. These monitored parameters were recorded on an 8-channel Sanborn direct writing recorder.

The electrophysiological and hemodynamic responses of the dogs were measured at a time before, and at various time intervals after, intravenous injection of a drug. Solutions of the drugs were administered rapidly as a single injection by means of a polyethylene catheter placed in the femoral vein.

The following vehicle formulations were used to solubilize the drugs for intravenous injection.

Formulation A

| Ingredient | per ml |
| --- | --- |
| Propylene glycol | 0.1 ml. |
| Benzyl Alcohol | 0.015 ml. |
| N-methylglucamine | 6.9 mg. |
| Water | q.s. to 1 ml. |

Formulation B

| Ingredient | per ml |
| --- | --- |
| Propylene glycol | 0.5 ml. |
| Ethyl alcohol | 0.1 ml. |
| Benzyl alcohol | 0.015 ml. |
| Water | q.s. to 1 ml. |

Formulation A contains N-methylglucamine, an agent which solubilizes antibiotics of the polyether type. This use of such an agent, included here for completeness although not part of this invention, is disclosed and claimed in a co-pending U.S. patent application Ser. No. 489,976 filed on even date herewith and described hereinabove.

Representative test compounds were evaluated for effects on heart rate, contractile force and mean arterial blood pressure. The results are set forth in the following Table.

Table I

| Active Ingredient | Vehicle Formulation | Dose, (mg/kg) (i.v.) | Time Post Drug, (Min.) | Inotropic Response (% change /Control) | Heart Rate (% change /Control) | Mean B.P. (% change/ Control) |
| --- | --- | --- | --- | --- | --- | --- |
| Antibiotic X-206 | A | 0.5 | 10 | 80 | 72 | 74 |
| Antibiotic X-206 | A | 0.5 | 15 | 83 | 48 | 100 |
| Antibiotic X-206, sodium salt | Water | 0.5 | 20 | 36 | 19 | 68 |
| " | A | 0.5 | 10 | 146 | 45 | 104 |
| " | Water | 1.0 | 5 | 0 | 6 | 15 |
| " | A | 1.0 | 10 | 43 | 27 | 34 |
| " | Water | 2.0 | 5 | 0 | 3 | 5 |
| " | Water | 4.0 | 5 | 0 | 3 | 2 |
| Antibiotic X-206, di-(N-methylglucamine) salt | Water | 0.5 | 20 | 100 | 27 | 97 |
| Nigericin, di-(N-methylglucamine) salt | Water | 0.5 | 15 | 56 | 47 | 37 |
| " | Water | 1.0 | 5 | 57 | 56 | 55 |
| " | Water | 2.0 | 5 | 71 | 52 | 11 |
| Monensin di(N-methyl-glucamine) salt | Water | 0.5 | 10 | 38 | 10 | 35 |
| " | Water | 0.1 | 10 | 83 | 23 | 110 |
| Monensin, sodium salt | Water | 0.5 | 30 | 69 | 4 | 41 |
| " | Water | 0.5 | 35 | 111 | 8 | 30 |
| " | Water | 1.0 | 30 | 121 | 14 | 37 |
| " | Water | 1.0 | 5 | 65 | −7 | 54 |
| " | Plasma | 1.0 | 25 | 116 | 4 | 44 |
| " | DMSO | 1.0 | 10 | 25 | 0 | −5 |
| " | B | 1.0 | 10 | 40 | 25 | 27 |
| " | Water | 1.0 | 10 | 13 | −2 | −5 |
| " | Water | 10.0 | 10 | 20 | 5 | 27 |
| Control | A | 0.05 | 5 | −18 | 0 | 0 |
| " | A | 0.10 | 5 | 0 | −4 | −3 |
| " | A | 0.20 | 15 | −13 | −4 | −2 |
| " | A | 0.30 | 5 | −11 | 0 | 3 |
| " | A | 0.40 | 5 | 25 | 4 | 9 |
| " | A | 0.80 | 15 | 25 | 0 | 6 |

The following examples illustrate the invention.

EXAMPLE 1

The following parenteral compositions were prepared.

| Ingredient | per ml | |
| --- | --- | --- |
| | I | II |
| Antibiotic X-206 | 10 mg. | — |
| Antibiotic X-206, sodium salt | — | 5.25 mg. |
| Propylene glycol | 0.1 ml. | 0.1 ml. |
| Benzyl alcohol | 0.015 ml. | 0.015 ml. |
| N-methylglucamine | 6.9 mg. | 6.9 mg. |
| Water | q.s. to 1 ml. | q.s. to 1 ml. |

The parenteral solutions exhibited cardiovascular activity when injected into dogs.

EXAMPLE 2

The following parenteral composition was prepared.

| Ingredient | per ml. |
| --- | --- |
| Monensin, sodium salt | 11.35 mg. |
| Propylene glycol | 0.5 ml. |
| Ethyl alcohol | 0.1 ml. |
| Benzyl alcohol | 0.015 ml. |
| Water | q.s. to 1 ml. |

This solution exhibited cardiovascular activity when injected into dogs.

I claim:

1. A method of therapeutic treatment by producing myocardial stimulation in a patient requiring such an effect which comprises administering to the patient an amount which is effective in producing myocardial stimulation, of antibiotic X-206, a compound represented by the formula

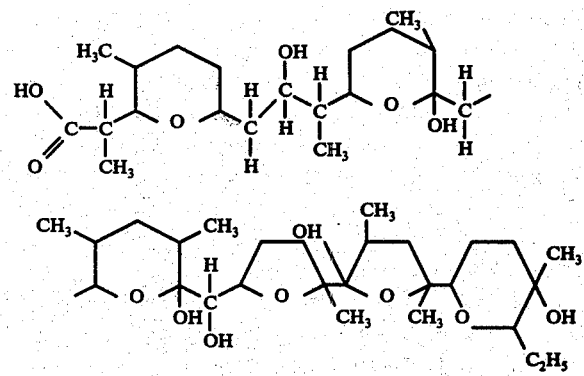

or pharmaceutically acceptable salts thereof.

* * * * *